(12) United States Patent
Hagg (10) Patent No.: US 10,695,120 B2
(45) Date of Patent: Jun. 30, 2020

(54) ADAPTER ELEMENT, HF SURGICAL INSTRUMENT, ADAPTER ATTACHMENT AND SYSTEM

(71) Applicant: ERBE ELEKTROMEDIZIN GMBH, Tuebingen (DE)

(72) Inventor: Martin Hagg, Wannweil (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 965 days.

(21) Appl. No.: 14/514,270

(22) Filed: Oct. 14, 2014

(65) Prior Publication Data

US 2015/0112323 A1  Apr. 23, 2015

(30) Foreign Application Priority Data

Oct. 18, 2013 (EP) .................................. 13189340

(51) Int. Cl.
| | | |
|---|---|---|
| *A61B 18/14* | (2006.01) | |
| *A61B 18/12* | (2006.01) | |
| *A61B 17/3203* | (2006.01) | |
| *A61B 18/00* | (2006.01) | |

(52) U.S. Cl.
CPC .......... *A61B 18/14* (2013.01); *A61B 18/1206* (2013.01); *A61B 17/3203* (2013.01); *A61B 2018/00708* (2013.01); *A61B 2018/141* (2013.01); *A61B 2018/1407* (2013.01); *A61B 2018/1412* (2013.01); *A61B 2018/1417* (2013.01); *A61B 2018/1495* (2013.01); *A61B 2218/002* (2013.01); *A61B 2218/003* (2013.01); *A61B 2218/008* (2013.01)

(58) Field of Classification Search
CPC ........ A61B 2218/003; A61B 2218/008; A61B 2018/00708; A61B 17/3203; A61B 18/14; A61B 18/1206; A61B 2018/1407; A61B 2018/141; A61B 2018/1412; A61B 2018/1495; A61B 2018/1417; A61B 2218/002

See application file for complete search history.

(56) References Cited

U.S. PATENT DOCUMENTS

| | | | | |
|---|---|---|---|---|
| 4,562,838 A | * | 1/1986 | Walker | ............... A61B 18/1402 219/230 |
| 5,088,997 A | * | 2/1992 | Delahuerga | .......... A61B 18/042 606/37 |
| 5,154,709 A | * | 10/1992 | Johnson | ............. A61B 18/1402 604/35 |

(Continued)

FOREIGN PATENT DOCUMENTS

| | | |
|---|---|---|
| AU | 2008203348 A1 | 2/2009 |
| DE | 10 2010 015 899 A1 | 8/2011 |

(Continued)

*Primary Examiner* — Jaymi E Della
(74) *Attorney, Agent, or Firm* — Blank Rome LLP (57) ABSTRACT

An adapter element for receiving an HF surgical handpiece is proposed. The adapter element is characterized in that it is possible by receiving the handpiece in the adapter element to form a smoke duct in said adapter element for discharging smoke from a treatment area, at least one stick-, point-, ring-, sphere- or loop-shaped electrode or combinations of the same being attached on the distal end of the adapter element.

20 Claims, 6 Drawing Sheets

(56) References Cited

U.S. PATENT DOCUMENTS

| | | | |
|---|---|---|---|
| 5,242,442 A * | 9/1993 | Hirschfeld | A61B 18/1402 604/35 |
| 5,431,650 A * | 7/1995 | Cosmescu | A61B 18/1402 604/22 |
| 5,451,223 A * | 9/1995 | Ben-Simhon | A61M 1/0084 604/35 |
| 5,674,219 A * | 10/1997 | Monson | A61B 18/1402 604/22 |
| 5,693,044 A * | 12/1997 | Cosmescu | A61B 18/042 604/35 |
| 5,707,402 A | 1/1998 | Heim | |
| 6,602,249 B1 * | 8/2003 | Stoddard | A61B 18/042 606/34 |
| 7,112,199 B2 | 9/2006 | Cosmescu | |
| 7,935,109 B2 | 5/2011 | Cosmescu | |
| 2003/0088247 A1 * | 5/2003 | Ineson | A61B 18/1402 606/42 |
| 2004/0122372 A1 * | 6/2004 | Jones | A61B 18/1477 604/162 |
| 2005/0119652 A1 | 6/2005 | Vetter et al. | |
| 2008/0058801 A1 * | 3/2008 | Taylor | A61B 18/042 606/45 |
| 2008/0154251 A1 * | 6/2008 | Stuart | A61B 18/203 606/13 |
| 2012/0303016 A1 * | 11/2012 | Fischer | A61B 18/1206 606/33 |

FOREIGN PATENT DOCUMENTS

| | | | |
|---|---|---|---|
| DE | 10 2010 060 336 A1 | 5/2012 | |
| GB | 2 406 793 A | 4/2005 | |
| JP | H08-98844 A | 4/1996 | |
| JP | H09-224951 A | 9/1997 | |
| JP | H11-318909 A | 11/1999 | |
| JP | 3318733 | * 8/2002 | A61B 18/12 |
| KR | 10-1073767 B1 | 10/2011 | |
| KR | 10 2012-0005995 A | 1/2012 | |
| WO | WO 96/23448 A1 | 8/1996 | |
| WO | WO 2011/095253 A1 | 8/2011 | |

* cited by examiner

ADAPTER ELEMENT, HF SURGICAL INSTRUMENT, ADAPTER ATTACHMENT AND SYSTEM

TECHNICAL FIELD

The invention relates to adapter elements for use with electrosurgery systems and/or high frequency (HF) surgical instruments.

BACKGROUND

HF surgical devices of the type addressed here are basically well-known. When using electrosurgical instruments, particularly when coagulating and cutting tissue with the help of high-frequency current, the treated tissue heats up very quickly. Smoke is generated as a result of the heating, whereby the smoke may include fine particles. The smoke arising consists not only of water vapor and aerosol but may also include carcinogenic and mutagenic constituents which may be hazardous to health for the people present in the operating theatre. It is therefore necessary during an electrosurgical application to evacuate smoke immediately at the place of origin to prevent excessive contamination of the environment, in particular the operating theatre and people located therein, and to reduce the associated hazards to health. Smoke evacuation systems have been created for this reason but they frequently deliver unsatisfactory results in respect of the suction power and moreover compromise the ergonomics of the electrosurgical instruments and even sometimes obstruct the view of the operating site.

SUMMARY

The object of embodiments of the present invention is therefore to create a smoke evacuation system in the form of an adapter element, an HF surgical instrument and an adapter attachment which provide optimum suction power with minimum impairment of the ergonomics and vision.

An adapter element is proposed for achieving the object referred to above. The adapter element is used for receiving an HF surgical handpiece and is characterized in that it is possible by receiving the handpiece in the adapter element to form a smoke duct in the adapter element for discharging smoke from a treatment area.

It may be important, therefore, that the smoke duct is only closed by assembling the adapter element with the handpiece and is formed by a region of the outer wall of the handpiece and a region of the inner wall of the adapter element. Not only is material saved in this way but assembling the adapter element with the HF surgical handpiece enables higher suction power of the smoke due to a larger cross-section of the smoke duct in addition to optimum ergonomics of the resulting HF surgical instrument. Moreover, the variably configured adapter element permits the use of a handpiece for virtually any HF surgical intervention and optimum smoke evacuation adapted thereto in each case. Thus different adapter elements, which in particular have different electrode shapes and smoke evacuators adapted thereto, can be provided for different purposes. Therefore, the appropriate instrument can be implemented for every purpose by combining the handpiece and the adapter element. Incidentally, the adapter elements may be disposable products which are disposed of after a single use.

Preferably at least one stick-, point-, ring-, sphere- or loop-shaped electrode is provided on the distal end of the adapter element. A plurality of electrodes may also be provided, in this case they may be combinations of the various electrode types referred to above. To further expand the application area of the adapter element, it may also be provided that, in addition to the at least one electrode, it also has a fluid jet applicator which can provide a fluid, e.g. water, for injecting or cutting tissue. The fluid jet applicator is preferably configured in such a way that the distal end of the electrode has an integrated nozzle for generating a fluid jet. In this case, the electrode therefore has an integrated fluid line and thus serves simultaneously as a fluid supply line. Alternatively, a fluid supply line may also be provided separately to the electrode. The HF surgical handpiece must then have, in addition to the power connection, a fluid connection which supplies a fluid to the fluid jet applicator.

Alternatively or if necessary additionally, the adapter element may have means for supplying gas, in particular inert gas. As a result of this, it is also possible with the surgical instrument according to embodiments of the invention to carry out argon plasma coagulation.

It is preferably provided that the smoke duct opens into a smoke lumen at the distal end of the adapter element. The smoke lumen is open towards a distal end of the at least one electrode and is used for admitting smoke arising in the vicinity of the electrode and for passing said smoke into the smoke duct. It is preferably provided that for the best possible smoke extraction the smoke lumen encircles the electrode at least in certain areas, it being possible to arrange the electrode and the smoke lumen concentrically or eccentrically to each other. It is particularly advantageous if the smoke lumen is adapted to the shape of the at least one electrode. For example, a hemispherical or funnel-shaped or conical smoke lumen may be provided for a spherical electrode, while a cylindrical smoke lumen, for example, may be provided for a stick electrode.

An elongated cavity which is used not only for receiving the handpiece but beyond this also for forming the smoke duct is preferably provided for receiving the handpiece in the adapter element. The cavity preferably has a bearing surface, in particular in the shape of at least one ledge, one shell or one protrusion for supporting the handpiece in or on the adapter element. For attachment of the handpiece, the adapter element preferably has a clip element, which is provided on the proximal end of the adapter element, for clipping or locking the handpiece in position. In this way, the HF surgical handpiece can be clipped particularly easily into the adapter element with a single motion sequence. It is also particularly advantageous if the adapter element is provided with a smoke detector, it being possible, for example, to arrange the smoke detector in the smoke lumen or in the smoke duct. At its proximal end the smoke duct preferably opens into a suction hose which is connected in turn to a suitable evacuation and filtering device.

In a preferred embodiment of the adapter element, the at least one electrode and the smoke lumen may be part of an adapter attachment which is interchangeably combinable with the adapter element. The advantage emerging as a result is that each electrode shape always cooperates with a smoke lumen adapted to said electrode shape such that it is possible to provide optimum suction power advantageously for the various electrode shapes during different applications. In this case, it is then not necessary to change the whole adapter element for different types of electrodes but rather to replace only the adapter attachment.

An HF surgical instrument which has an HF surgical handpiece and an adapter element for receiving said handpiece, in particular according to embodiments of the invention, is proposed for achieving the object referred to above.

The HF surgical instrument is characterized in that an inner wall region of the adapter element and an outer wall region of the handpiece delimit a smoke duct in the assembled state of said adapter element and said handpiece. As a result of this, particularly high smoke suction power is accomplished as the smoke duct can have a larger diameter without compromising the ergonomics of the surgical instrument and obstructing the view of the operating site.

It is particularly advantageous if a preferably completely peripheral (closed) seal can be disposed between the adapter element and the handpiece. In this case, a particularly tight, in particular a gas-tight, seal can be made between the adapter element and the handpiece. The handpiece preferably has at least one power connection and also, if necessary, at least one fluid connection. If both a power connection and also a fluid connection and an appropriate fluid jet applicator are provided, it is possible with a single multifunctional HF surgical instrument to implement both a monopolar cutting procedure and also a water jet application (e.g. injection of tissue) without changing instruments. The handpiece preferably has a switching device for controlling the supply of power and/or fluid. It is particularly advantageous if an adjusting device for moving an extendable and retractable electrode is additionally provided.

An adapter attachment for interchangeable combination with an HF surgical handpiece with integrated smoke extraction and/or an adapter element with a smoke duct for receiving an HF surgical handpiece is proposed for achieving the object referred to above, the adapter attachment having at least one electrode and one smoke lumen.

For combining the adapter attachment with a handpiece or an adapter element, the proximal end of the adapter attachment is preferably adapted to the shape of the respective distal end of the handpiece or the adapter element such that a positive-fit connection is formed between the two parts. In addition, a connection device, for example in the shape of locking recesses, a threaded connection or a magnetic connection is preferably provided, said device being disposed on the adapter attachment and being used for connecting to an HF surgical handpiece and/or an adapter element for receiving an HF surgical handpiece. In particular, the adapter elements may be disposable products which are disposed of after a single use.

An adapter attachment may have at least one electrode which may be stick-, point-, ring-, sphere- or loop-shaped. Furthermore, combinations of a plurality of the aforementioned electrode types may also be provided, the at least one electrode preferably being movably supported such that the electrode tip can therefore protrude more or less far out of the smoke lumen.

Beyond this, the adapter attachment may be configured in such a way that it fulfils a dual function. Thus, in addition to the electrode, a fluid jet applicator may be provided which in particular is configured in such a way that the distal end of the electrode has an integrated nozzle for generating a fluid jet. In this case, it is possible to implement two different surgical applications with a single adapter attachment without changing instruments or changing the adapter attachment. For example, it is possible with the electrode to coagulate or cut and to inject tissue by applying a very fine water jet.

A set is also proposed for achieving the object referred to above. The set comprises the following components: at least one adapter attachment with at least one electrode and a smoke lumen, at least one handpiece with at least one power connection and, if necessary, with at least one fluid connection; and either at least one smoke duct integrated in the handpiece or attached thereto or alternatively an adapter element for receiving the handpiece which has a smoke duct. In both alternatives, the smoke duct preferably cooperates in the set's assembled state with the smoke lumen of the adapter attachment to implement optimum smoke extraction.

In addition, an electrosurgery system having an HF surgical instrument and an HF generator which is connected to or is combinable with the HF surgical instrument is disclosed. The HF surgical instrument is configured according to embodiments of the invention. The embodiments disclosed in this application may be developed accordingly.

Embodiments of the invention are explained in greater detail in the specification and drawings.

BRIEF DESCRIPTION OF THE DRAWINGS

FIG. 6b is a longitudinal section of the HF surgical instrument according to FIG. 6a;

FIG. 6c is a longitudinal section along the section line A-A according to FIG. 6b;

FIG. 7a is a perspective view of an HF surgical instrument according to a seventh embodiment of the invention;

FIG. 7b is a longitudinal section of the HF surgical instrument according to FIG. 7a;

FIG. 7c is a cross-section along the section line A-A according to FIG. 7b;

FIG. 7d is an enlarged detailed view of a detail according to FIG. 7c;

FIG. 8b is a longitudinal section of the HF surgical instrument according to FIG. 8a;

FIG. 8c is a cross-section along the section line A-A according to FIG. 8b;

FIG. 14 is a perspective view of an HF surgical instrument according to a fourteenth embodiment of the invention;

FIG. 15a is a longitudinal section of an adapter attachment according to an embodiment of the invention; and FIG. 15b is a cross-section of the adapter attachment along the section line B-B according to FIG. 15a.

DETAILED DESCRIPTION

Figure 1:
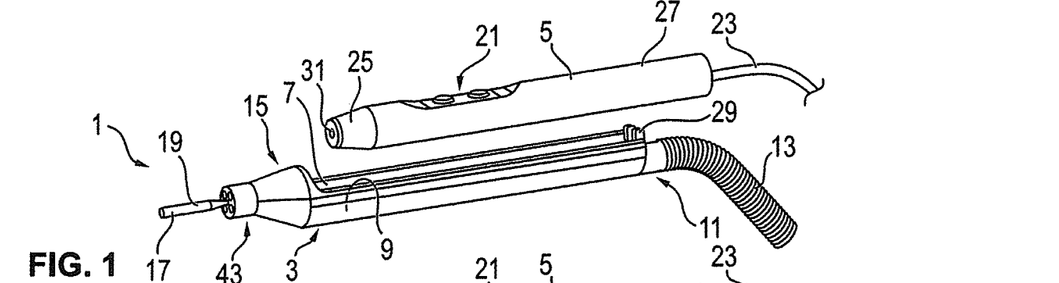
FIG. 1 is a perspective view of an HF surgical instrument according to a first embodiment of the invention.

FIG. 1 shows a perspective view of an HF surgical instrument 1 according to a first embodiment of the invention. The HF surgical instrument 1 comprises an adapter element 3 for receiving an HF surgical handpiece 5. The adapter element 3 is essentially elongated and in particular adapted to the contour of the handpiece 5 in such a way that the ergonomics of the resulting HF surgical instrument are not compromised. In addition, the adapter element 3 has a cavity 7 for receiving the handpiece 5 and for forming a smoke duct 9 (see FIG. 6b).

Provided at a proximal end 11 of the adapter element 3 is a suction hose 13 which on one side is in fluid communication with the cavity 7 and on the other side is connected to an extraction device, such as a pump or similar and a filter device (not shown in the Figure). At its distal end 15, the adapter element 3 has, by way of example, a stick-shaped electrode 17 and a smoke lumen 19 for admitting smoke arising in the vicinity of the electrode, the electrode 17 extending through the smoke lumen 19.

Figure 3:
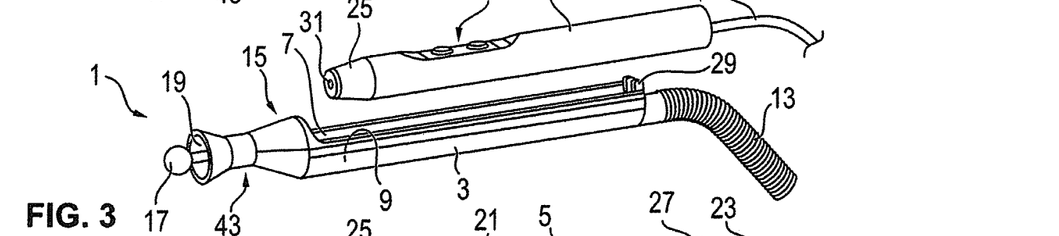
FIG. 3 is a perspective view of an HF surgical instrument according to a third embodiment of the invention.
Figures 4, 5:
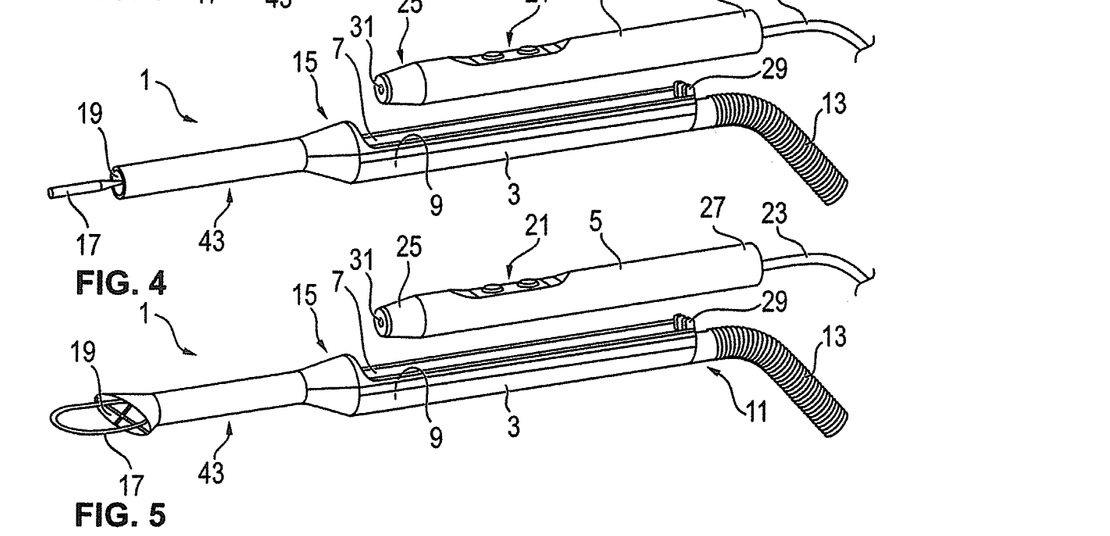
FIG. 4 is a perspective view of an HF surgical instrument according to a fourth embodiment of the invention.
FIG. 5 is a perspective view of an HF surgical instrument according to a fifth embodiment of the invention.

The smoke lumen 19 is open at its distal end, i.e. on the side directed towards the distal electrode, and in this way can admit smoke during treatment. Starting from the smoke lumen 19, the smoke is sucked through the smoke duct 9 and the suction hose 13 and disposed of in an appropriate filtration system. The smoke lumen is configured advantageously such that it is adapted to the electrode shape in each case. This situation becomes apparent particularly as a result of the other FIGS. 2-5 which illustrate the adapter elements with different smoke lumens 19 and different electrodes 17, in each case the shape of the smoke lumen 19 being adapted in an optimum manner to the shape of the electrode in order to admit smoke arising in the vicinity of the electrode as completely as possible. Thus, in FIG. 2 for example, the smoke lumen 19 is configured as an elongated slot while in FIG. 3 there is a funnel-shaped or conical configuration which widens towards the spherical electrode 17. This also applies correspondingly for FIG. 4 where an essentially cylindrical smoke lumen 19 encircles a stick-shaped electrode 17 at least in certain areas, and for FIG. 5 in which an essentially oval funnel-shaped smoke lumen 19 is assigned to a loop-shaped electrode.

The handpiece 5 comprises a switching device 21 for controlling the supply of power and/or fluid to the electrode 17 of the adapter element. If the electrode 17 is designed to be movable in a longitudinal direction, the handpiece 5 may additionally have an adjusting device for moving the electrode manually or electrically. Furthermore, the handpiece 5 has a power connection 23 which is connected to an HF generator to supply the electrode 17 with an HF current. If the HF surgical instrument 1 additionally has a fluid jet applicator, a fluid connection (not illustrated in the Figure) may be provided in addition to the power connection 23.

For connecting the handpiece 5 to the adapter element 3, said handpiece 5 must be inserted into the cavity 7 of said adapter element 3. In doing so, the distal end 25 of the handpiece 5 is first introduced into the cavity 7, which serves as an abutment for the distal end 25 of the handpiece 5, in the distal region 15 of the adapter element 3. Subsequently, the proximal end 27 of the handpiece 5 is pressed downwards into the cavity 7 until the handpiece 5 cooperates with the clip element 29 and the handpiece 5 and the handpiece 5 is therefore firmly anchored in the adapter element 3.

The clip element 29 may, for example, be a prestressed flexible clamping element which fastens the power connection 23 to the adapter element 3. By means of an appropriate effort that is exerted on the handpiece 5, it can then be removed again from the adapter element 3. Basically, other fastening options are also conceivable for fastening the handpiece 5 in the adapter element 3. A magnetic holder, for example, is conceivable. It is crucial that the handpiece 5 can be joined to the adapter element 3 particularly easily by means of a single motion sequence.

For connecting the power connection 23 to the electrode 17, the handpiece 5 additionally has a connection 31 into which the proximal end of the electrode 17 is inserted while clipping the handpiece 5 into the adapter element 3. In this way, it is possible to establish an electrical connection between an HF generator not shown in the Figure and the electrode 17. If necessary, an appropriate fluid connection is additionally provided if the electrode is simultaneously configured as a water jet applicator or if a fluid supply duct that is independent of the electrode is provided.

Overall, FIGS. 1-5 show that a handpiece 5 with variously configured adapter elements 3 can be combined for the widest range of applications with only a single hand movement. It is particularly advantageous in this case that a smoke duct is only created by joining the handpiece 5 to the adapter element 3 which cooperates with a smoke lumen 19 that is adapted in each case to the associated electrode shape. In this way, a large smoke duct volume is created overall and therefore optimum smoke extraction is achieved.

Figure 2:
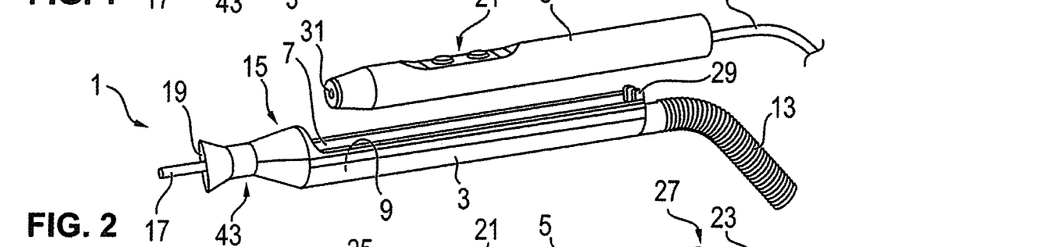
FIG. 2 is a perspective view of an HF surgical instrument according to a second embodiment of the invention.
Figures 6A, 6D:
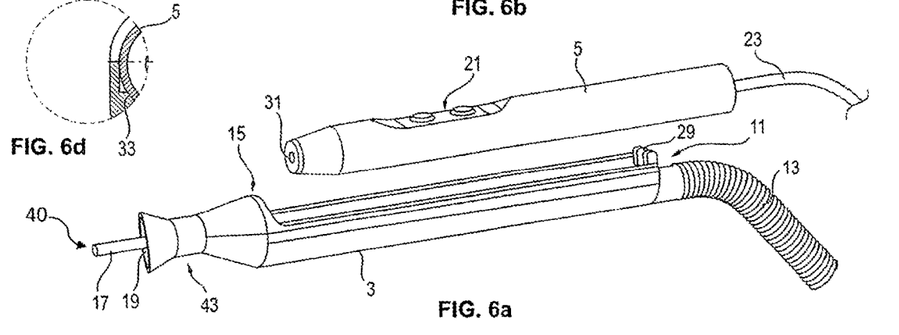
FIG. 6a is a perspective view of an HF surgical instrument according to a sixth embodiment of the invention.
FIG. 6d is an enlarged detailed view of a detail according to FIG. 6c.
Figures 6B, 6C:
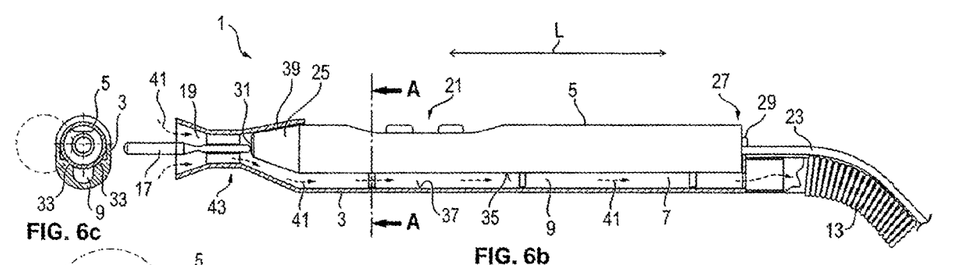

FIG. 6a shows a perspective view of the embodiment according to FIG. 2 while FIG. 6b shows a longitudinal section through the corresponding HF surgical instrument 1 in which the handpiece 5 is thus clipped into the adapter element 3.

FIG. 6b makes it clear that the elongated contour of the adapter element 3 is adapted to the essentially cylindrical and also elongated configuration of the handpiece 5. The cavity 7 is configured essentially in a half-shell shape for receiving the handpiece 5. For supporting the handpiece 5 in the cavity 7, the adapter element 3 has a bearing surface 33 on which the handpiece 5 can be supported. After inserting the handpiece 5 in the adapter element 3, the smoke duct 9 is formed by an outer wall region 35 of the handpiece 5 and an inner wall region 37 of the adapter element 3.

The handpiece 5 is held securely in the adapter element 3 by the retaining region 39 at the distal end 15 which serves as an abutment for the distal end 25 of the handpiece 5. The proximal end 27 of the handpiece 5 by comparison is fastened to the adapter element 3 using the clip element 29. At the same time, the retaining region 39 is adapted in such a manner to the distal end 25 of the handpiece 5 that a positive fit occurs when the handpiece 5 is inserted into the adapter element 3. To ensure particularly easy insertion of the handpiece 5 into the retaining region 39, the distal end 25 of the handpiece 5 is preferably conical in design. In other words, the handpiece 5 has a smaller diameter at its distal end than in the other regions. The retaining region 39 is designed complementary to this and in this way can effortlessly accommodate the distal end 25 of the handpiece 5.

FIG. 6b makes it even clearer that smoke arising in the operating site is sucked into the smoke lumen 19 along the arrow 41 and from there it is conducted further along the arrow 41 through the smoke duct 9 between the handpiece 5 and the adapter element 3 and finally to the suction hose 13.

Finally, FIG. 6b also makes it clear that the electrode 17 is held essentially centrically in a connecting piece 43 of the adapter element, in particular by means of suitable retaining ribs, and thus extends through the connecting piece 43. The present smoke lumen 19 arranged in a funnel shape for admitting the smoke is provided at the distal end of the connecting piece 43. As also becomes clear, particularly in conjunction with FIGS. 4 and 5, the length of the connecting piece 43 may vary and consequently be configured differently for different application purposes. A telescopically variable length of the connecting piece 43 is also conceivable in principle.

FIG. 6c additionally makes it clear that the bearing surface 33 for supporting the handpiece 5 is essentially shell-shaped in the embodiment illustrated in FIGS. 6a-6d, it not being imperative for the bearing surface to be formed full-surface along the longitudinal direction L of the HF surgical instrument. Basically, it is also even conceivable for the arrangement of a plurality of ribs disposed at a distance from each other, said ribs obstructing the flow of smoke along the arrow 41 in the smoke duct 9 as little as possible.

Figures 7A, 7B, 7C, 7D:
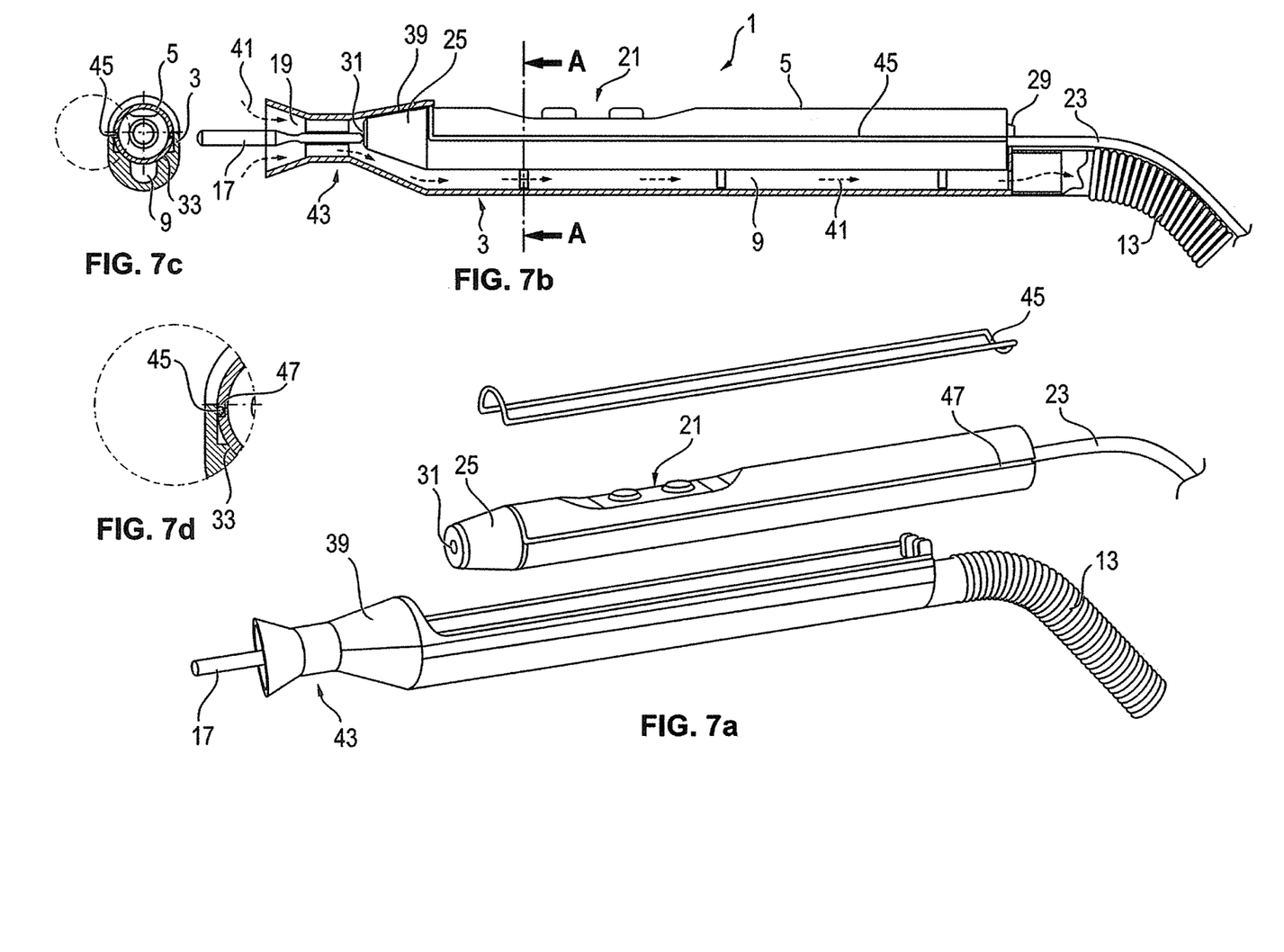
Figures 8A, 8D:
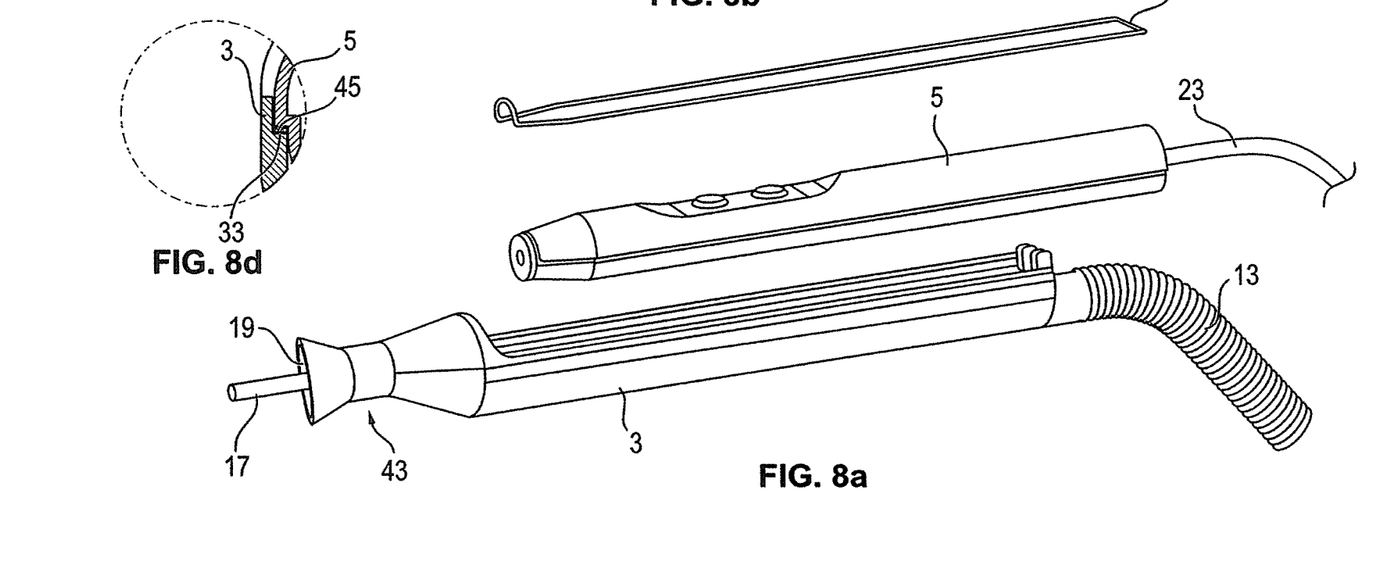
FIG. 8a is a perspective view of an HF surgical instrument according to an eighth embodiment of the invention.
FIG. 8d is an enlarged detailed view of a detail according to FIG. 8c.
Figures 8B, 8C:
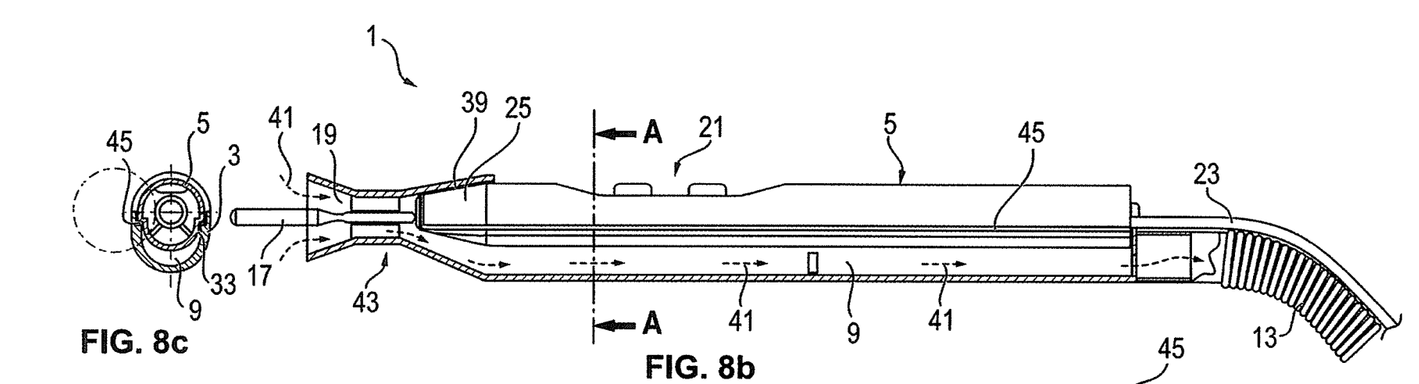

FIGS. 7a-7d show another embodiment of the invention in which a seal 45 is provided between the handpiece 5 and the adapter element 3, said seal being peripherally closed and ensuring a (gas-tight) termination of the joint between the handpiece 5 and the adapter element 3. The handpiece 5 may have a receiving groove 47 (as shown in FIG. 7a) configured according to the shape of the seal for accommodating said seal 45. However, it is also basically conceivable to provide a corresponding receiving groove in the region of the inner wall of the adapter element 3. As FIG. 7d in particular makes clear, in the assembled state of the handpiece 5 and the adapter element 3, the seal 45 lies between the inner wall 37 of the adapter element 3 and the outer wall 35 of the handpiece 5 and therefore ensures sealing of the smoke duct to the outside.

FIGS. 8a-8d show yet another embodiment of an HF surgical instrument 1, in which the inner wall of the adapter element 3 has a step running in the longitudinal direction L, on which step a complementary step of the handpiece 5 is supported. In the embodiment according to FIGS. 8a-8d, support is therefore provided in the form of bearing surfaces 33 which are configured as steps and thus enable the formation of a significantly enlarged smoke duct cross-section. In this embodiment of the invention a seal 45 is also provided which is preferably disposable between the handpiece 5 and the adapter element 3 in the region of the step-shaped bearing surface 33.

FIGS. 9-14 additionally show different examples of embodiments of the invention in which the connecting piece 43 is not configured integrally with the adapter element 3 but rather is combinable, in the form of an adapter attachment 49, which is interchangeable with the adapter element 3 and/or with a conventional handpiece 5, in particular with a handpiece with integrated smoke duct or a handpiece with a smoke duct attachable thereto.

Figure 9:
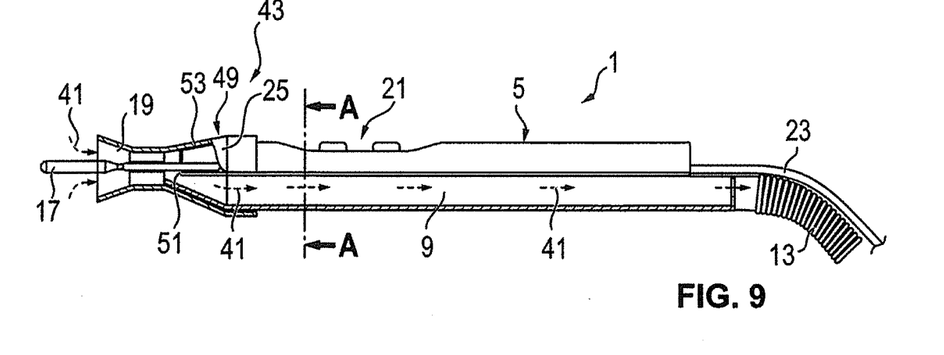
FIG. 9 is a longitudinal section through an HF surgical instrument according to a ninth embodiment of the invention.
Figure 10:
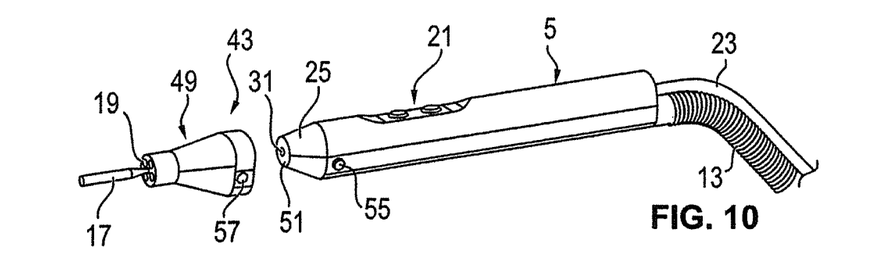
FIG. 10 is a perspective view of an HF surgical instrument according to a tenth embodiment of the invention.
Figure 11:
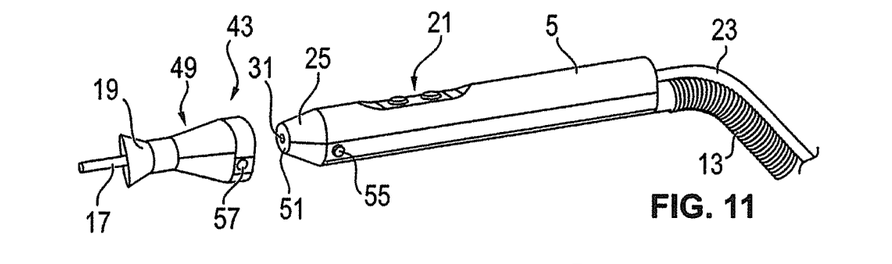
FIG. 11 is a perspective view of an HF surgical instrument according to an eleventh embodiment of the invention.
Figure 12:
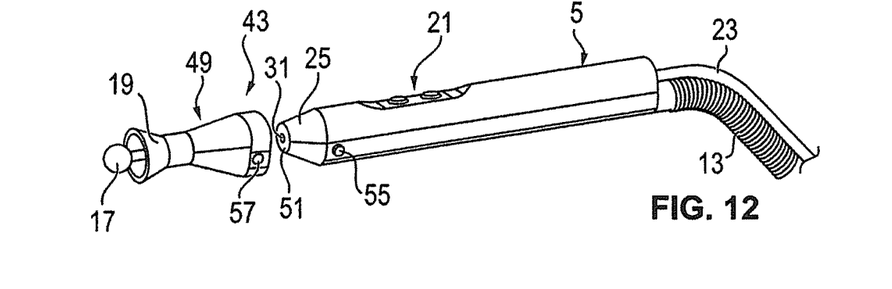
FIG. 12 is a perspective view of an HF surgical instrument according to a twelfth embodiment of the invention.

FIG. 9 shows a longitudinal section through an HF surgical instrument 1 with a handpiece 5 and a smoke duct 9 integrated therein which, for example, may also be configured as a hose that has an opening 51 on the distal end 25 of the handpiece 5 enabling fluid communication with the adapter attachment 49. The adapter attachment 49 comprises, like the connecting piece 43 of FIGS. 1-8, an electrode 17 which, for example, is held centrically or eccentrically inside the adapter attachment 49 with the aid of ribs or similar fastening means, and which protrudes out of a smoke lumen 19.

The adapter attachment 49 is pushed onto the handpiece 5 such that the proximal end 53 engages in the electrical connection 31 of the handpiece 5 in order to establish an electrical connection between an HF generator and the electrode 17. As FIG. 9 shows, the proximal end of the adapter attachment 49 is adapted to the shape of the distal end 25 of the handpiece 5 such that a positive fit occurs when the two pieces are joined. In this case too, a seal may be provided which is disposed preferably completely peripherally in the joining region between the handpiece 5 and the adapter attachment 49.

Fixing of the adapter attachment 49 to the handpiece 5 can be achieved by means of appropriate fastening means. In FIGS. 9-14, a variant is illustrated by way of example in which the adapter attachment 49 can simply be clipped onto the handpiece 5 by inserting locking elements 55 provided on the handpiece 5 into corresponding locking recesses 57 of the adapter attachment 49. Provided that the locking elements 55 are spring-loaded or flexible, the adapter attachment 49 can easily be detached from the handpiece 5, for example, if an electrode with a different shape is required for a different surgical intervention. Alternatively, it may also be provided that magnetic or similar fastening means are provided on the adapter attachment 49 and on the handpiece 5 for combining the two parts.

Figure 13:
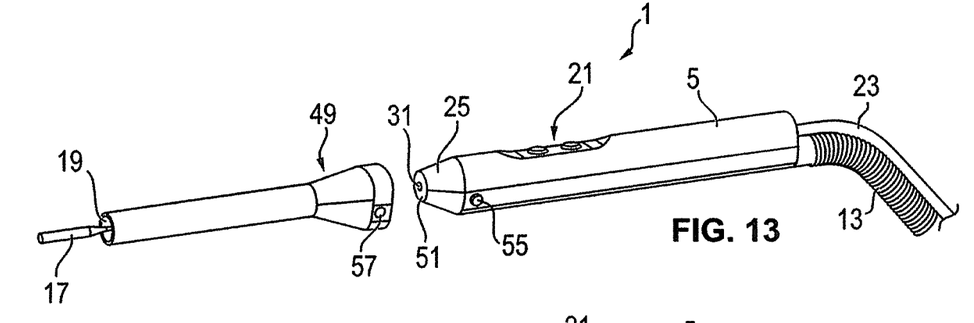
FIG. 13 is a perspective view of an HF surgical instrument according to a thirteenth embodiment of the invention.
Figures 14, 15A, 15B:
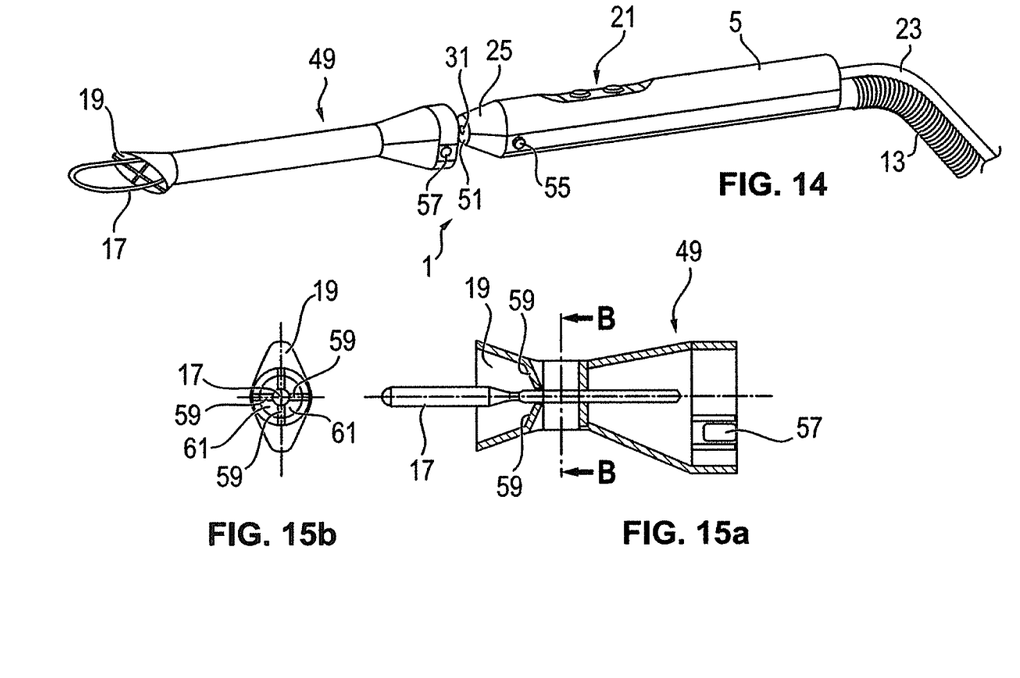

FIGS. 13 and 14 show further embodiments of an adapter attachment 49 which are significantly longer than the examples according to FIGS. 9-12. Thus overall it can be seen that the adapter attachment 49 may be configured for many different applications with different lengths, different electrodes and different smoke lumens. Replacement is particularly easy by simply clipping the attachment onto a handpiece 5. Basically, the adapter attachment 49 may also have a fluid jet applicator. This may, for example, be in the form of a nozzle (e.g., nozzle 40 of FIG. 6a) integrated in the electrode or may also be configured separately from the electrode in the adapter attachment 49. In case the adapter attachment 49 is to be used for carrying out a fluid application (normally water application), it is clear that the handpiece 5 may have an appropriate fluid supply line and appropriate control means. Incidentally, the embodiment of the invention shown in FIGS. 9-14 may also have an electrode 17 which is variable in length and thus may protrude more or less far out of the adapter attachment 49. Appropriate control means in this case are preferably provided on the handpiece 5 such that the electrode 17 can be moved manually or also electrically.

The adapter attachment 49 is not only provided with an integrated smoke duct 9 for the one-piece embodiment of the handpiece 5 shown in FIGS. 9-14 but it is also basically conceivable to combine the adapter attachment 49 with an adapter element 3 according to FIGS. 1-8 such that on one hand the adapter element 3 can be configured for different handpieces 5 while the adapter attachment 49 is configured to be suitable for every adapter element 3. Thus, while a standard interface may exist between the adapter attachment 49 and the adapter element 3, different adapter elements 3 may be adapted for different handpieces 5, in particular to different shapes and dimensions. An appropriate HF surgical set may then, for example, have one or more adapter attachments, one or more adapter elements (adapter shell) and one or more handpieces 5.

FIG. 15a shows a longitudinal section through an adapter attachment 49, while FIG. 15b shows a cross-section along the section line B-B of FIG. 15a. FIGS. 15a and 15b make it clear that the electrode 17 can be held inside the adapter attachment 49 with the aid of ribs 59 which, on one hand, are in contact with the inner wall of the adapter attachment 49 and, on the other hand, form an annular opening for receiving the electrode 17. Formed between the individual ribs are openings 61 which enable smoke sucked into the smoke lumen 19 to pass through the opening 51 of the handpiece 5 and from there into the smoke duct 9.

Embodiments of the present invention create an advantageous smoke extraction system which, as a result of its modular design, is not only flexibly adaptable to many different HF surgical applications (in particular also combined applications using current and fluid) but which moreover enables optimum suction power with minimum obstruction of the ergonomics and view of the operating site for each individual electrosurgical application.

What is claimed as new and desired to be protected by Letters Patent of the United States is:

1. An adapter element for receiving a high-frequency (HF) surgical handpiece having a proximal-most end the adapter element comprising:
    a trough-shaped body having a cavity and for receiving the proximal-most end of the HF surgical handpiece to thereby form a smoke duct in the cavity along a length of the RF surgical handpiece between the body and the HF surgical handpiece for discharging smoke from a treatment area; and
    a stick-shaped, point-shaped, ring-shaped, sphere-shaped or loop-shaped electrode connected to the body.

2. The adapter element of claim 1, wherein the electrode is movably supported by the body.

3. The adapter element of claim 1, wherein the adapter element further comprises a fluid jet applicator configured as a nozzle integrated into a distal end of the electrode for generating a fluid jet.

4. The adapter element according to claim 1, wherein the smoke duct is formed at a distal end of the adapter element and opens into a smoke lumen.

5. The adapter element of claim 4, wherein the smoke lumen is open towards a distal end of the electrode and encircles said electrode either concentrically or eccentrically at least in certain areas.

6. The adapter element of claim 4, wherein a shape of the smoke lumen is adapted to a shape of the electrode and is configured to be essentially cylindrical or conical.

7. The adapter element of claim 4, wherein a smoke detector is arranged in the smoke lumen or in the smoke duct.

8. The adapter element of claim 1, wherein the cavity has a bearing surface having at least one ledge, at least one rib or at least one shell for supporting the HF surgical handpiece.

9. The adapter element of claim 1, wherein a clip element is provided on the proximal end of the adapter element for clipping or locking in position the HF surgical handpiece on the adapter element.

10. The adapter element of claim 1, wherein the smoke duct opens into a suction hose which is connected to a proximal end of the adapter element.

11. An HF surgical instrument comprising the adapter element of claim 1 for receiving the HF surgical handpiece, wherein an inner wall region of the body of the adapter element and an outer wall region of the HF surgical handpiece delimit the smoke duct in an assembled state of the adapter element and the HF surgical handpiece.

12. The HF surgical instrument of claim 11, wherein a preferably peripheral seal is disposable between the adapter element and the HF surgical handpiece.

13. The HF surgical instrument of claim 11, wherein the HF surgical handpiece has at least one power connection and/or at least one fluid connection.

14. The HF surgical instrument according to claim 11, wherein the HF surgical handpiece comprises:
    a switching device for controlling power; and
    an adjusting device for moving the electrode.

15. An electrosurgery system comprising the HF surgical instrument according to claim 11; and an HF generator configured to connect to the HF surgical instrument.

16. A set comprising:
    at least one HF surgical handpiece with at least one power connection and at least one fluid connection, the at least one HF surgical handpiece having a proximal-most end and
    at least one adapter element comprising:
        a trough-shaped body having a cavity and for receiving the proximal-most end of the at least one HF surgical handpiece to thereby form a smoke duct in the cavity along a length of the at least one HF surgical handpiece between the at least one adapter element and the at least one HF surgical handpiece for discharging smoke from a treatment area; and
        a stick-shaped, point-shaped, ring-shaped, sphere-shaped or loop-shaped electrode connected to the body.

17. The set of claim 16, further comprising at least one adapter attachment configured to connect to a distal end of one or more of the at least one adapter elements.

18. An HF surgical instrument comprising:
    an HF surgical handpiece having a proximal-most end
    an adapter element comprising a trough-shaped body having a cavity and for receiving the proximal-most end of the HF surgical handpiece and a stick-shaped, point-shaped, ring-shaped, sphere-shaped or loop-shaped electrode connected to the body; and
    a smoke duct arranged in the cavity along a length of the HF surgical handpiece between the body of the adapter element and the HF surgical handpiece for discharging smoke from a treatment area.

19. The HF surgical instrument of claim 18, further comprising a fluid jet applicator configured as a nozzle integrated into a distal end of the electrode for generating a fluid jet.

20. An electrosurgery system comprising the HF surgical instrument of claim 19; and an HF generator configured to connect to the HF surgical instrument.

* * * * *